United States Patent
Salvo et al.

(10) Patent No.: US 8,303,818 B2
(45) Date of Patent: Nov. 6, 2012

(54) METHOD AND APPARATUS USING AN ACTIVE IONIC LIQUID FOR ALGAE BIOFUEL HARVEST AND EXTRACTION

(75) Inventors: Roberto Di Salvo, Madison, AL (US); Alton Reich, Huntsville, AL (US); H. Waite H. Dykes, Jr., Huntsville, AL (US); Rodrigo Teixeira, Madison, AL (US)

(73) Assignee: Streamline Automation, LLC, Huntsville, AL (US)

( * ) Notice: Subject to any disclaimer, the term of this patent is extended or adjusted under 35 U.S.C. 154(b) by 0 days.

(21) Appl. No.: 12/970,512

(22) Filed: Dec. 16, 2010
(Under 37 CFR 1.47)

(65) Prior Publication Data

US 2011/0076748 A1   Mar. 31, 2011

Related U.S. Application Data

(60) Provisional application No. 61/358,322, filed on Jun. 24, 2010.

(51) Int. Cl.
*B01D 11/02*  (2006.01)
*C12N 1/12*   (2006.01)
*B01D 11/04*  (2006.01)
*C02F 1/26*   (2006.01)

(52) U.S. Cl. ........ 210/634; 210/639; 210/638; 210/752; 435/257.1

(58) Field of Classification Search .................. None
See application file for complete search history.

(56) References Cited

U.S. PATENT DOCUMENTS

| | | |
|---|---|---|
| 1,943,176 A | 1/1934 | Basel |
| 2,393,293 A | 1/1946 | Corley |
| 3,632,330 A | 1/1972 | Michaelson |
| 3,753,362 A | 8/1973 | Kerst |
| 3,871,861 A | 3/1975 | Merianos |
| 4,065,875 A | 1/1978 | Srna |
| 4,189,311 A | 2/1980 | Laqua |
| 4,328,118 A | 5/1982 | Friedmann |
| 4,554,390 A | 11/1985 | Curtain |
| 5,413,722 A | 5/1995 | Eastman |
| 5,783,091 A | 7/1998 | Werle |
| 5,801,050 A | 9/1998 | Uchida |
| 5,910,254 A | 6/1999 | Guelcher |
| 5,951,875 A | 9/1999 | Kanel |
| 5,994,383 A | 11/1999 | Dyer |

(Continued)

OTHER PUBLICATIONS

Sigma Aldrich, "Product Comparison", available through a catalog search on <www.sigmaaldrich.com>, accessed Apr. 23, 2011, pp. 1-3.*

(Continued)

*Primary Examiner* — Vickie Kim
*Assistant Examiner* — Katherine Zalasky
(74) *Attorney, Agent, or Firm* — KIPA AB; Tomas Friend (57) ABSTRACT

The invention relates to use of an active ionic liquid to dissolve algae cell walls. The ionic liquid is used to, in an energy efficient manner, dissolve and/or lyse an algae cell walls, which releases algae constituents used in the creation of energy, fuel, and/or cosmetic components. The ionic liquids include ionic salts having multiple charge centers, low, very low, and ultra low melting point ionic liquids, and combinations of ionic liquids. An algae treatment system is described, which processes wet algae in a lysing reactor, separates out algae constituent products, and optionally recovers the ionic liquid in an energy efficient manner.

20 Claims, 8 Drawing Sheets

U.S. PATENT DOCUMENTS

| | | |
|---|---|---|
| 6,000,551 A | 12/1999 | Kanel |
| 6,010,996 A | 1/2000 | Hu |
| 6,180,376 B1 | 1/2001 | Lidell |
| 6,291,397 B1 | 9/2001 | Wilkins |
| 6,524,486 B2 | 2/2003 | Borodyanski |
| 6,808,557 B2 | 10/2004 | Holbrey |
| 6,824,599 B2 | 11/2004 | Swatloski |
| 7,122,505 B1 | 10/2006 | Unhoch |
| 7,300,585 B1 * | 11/2007 | Holzwarth et al. ............ 210/666 |
| 7,662,616 B2 | 2/2010 | Hazlebeck |
| 7,682,821 B2 | 3/2010 | Woods |
| 7,687,261 B2 | 3/2010 | Hazlebeck |
| 7,736,508 B2 | 6/2010 | Limcaco |
| 7,763,457 B2 | 7/2010 | Dunlop |
| 7,763,724 B2 | 7/2010 | Kang |
| 7,776,211 B2 | 8/2010 | Limcaco |
| 7,777,085 B2 | 8/2010 | Berry et al. |
| 7,824,904 B1 | 11/2010 | Dimanshteyn |
| 2003/0001439 A1 | 1/2003 | Schur |
| 2004/0040913 A1 | 3/2004 | Oberlander |
| 2004/0144338 A1 | 7/2004 | Goldman |
| 2005/0115893 A1 | 6/2005 | Brune |
| 2005/0262588 A1 | 11/2005 | Dehesh |
| 2006/0241287 A1 * | 10/2006 | Hecht et al. ................... 530/356 |
| 2007/0048848 A1 | 3/2007 | Sears |
| 2007/0161095 A1 | 7/2007 | Gurin |
| 2007/0191303 A1 | 8/2007 | Dillon |
| 2007/0196894 A1 | 8/2007 | Sim |
| 2008/0000436 A1 | 1/2008 | Goldman |
| 2008/0044887 A1 | 2/2008 | Maltezos |
| 2008/0090284 A1 | 4/2008 | Hazlebeck |
| 2008/0096267 A1 | 4/2008 | Howard |
| 2008/0135474 A1 | 6/2008 | Limcaco |
| 2008/0135475 A1 | 6/2008 | Limcaco |
| 2008/0149550 A1 | 6/2008 | Suarez |
| 2008/0155888 A1 | 7/2008 | Vick |
| 2008/0160591 A1 | 7/2008 | Wilson |
| 2008/0178739 A1 | 7/2008 | Lewnard |
| 2008/0182298 A1 | 7/2008 | Day |
| 2008/0188676 A1 | 8/2008 | Anderson |
| 2008/0220486 A1 | 9/2008 | Weiss |
| 2008/0220515 A1 | 9/2008 | McCall |
| 2008/0299633 A1 | 12/2008 | Rush |
| 2009/0011492 A1 | 1/2009 | Berzin |
| 2009/0023180 A1 | 1/2009 | Dillon |
| 2009/0029445 A1 | 1/2009 | Eckelberry |
| 2009/0047721 A1 | 2/2009 | Trimbur |
| 2009/0056201 A1 | 3/2009 | Morgan |
| 2009/0071064 A1 | 3/2009 | Machacek |
| 2009/0077864 A1 | 3/2009 | Marker et al. |
| 2009/0081742 A1 | 3/2009 | Dunlop |
| 2009/0119980 A1 | 5/2009 | Walker |
| 2009/0130706 A1 | 5/2009 | Berzin |
| 2009/0151240 A1 | 6/2009 | Kayama |
| 2009/0181440 A1 | 7/2009 | Rush |
| 2009/0203116 A1 | 8/2009 | Bazaire |
| 2009/0230040 A1 | 9/2009 | Limcaco |
| 2009/0234146 A1 * | 9/2009 | Cooney et al. ................ 554/174 |
| 2009/0291490 A1 | 11/2009 | Spradling |
| 2009/0298158 A1 | 12/2009 | Thomas |
| 2009/0298159 A1 | 12/2009 | Wu |
| 2009/0301399 A1 | 12/2009 | Brown et al. |
| 2009/0314193 A1 | 12/2009 | Groves et al. |
| 2009/0317901 A1 | 12/2009 | Vance |
| 2010/0003739 A1 | 1/2010 | Duhring |
| 2010/0050502 A1 | 3/2010 | Wu |
| 2010/0055765 A1 | 3/2010 | Frank |
| 2010/0068776 A1 | 3/2010 | Woods |
| 2010/0068801 A1 | 3/2010 | Woods |
| 2010/0077654 A1 | 4/2010 | Wu |
| 2010/0081835 A1 | 4/2010 | Wu |
| 2010/0093078 A1 | 4/2010 | Wang |
| 2010/0144017 A1 | 6/2010 | Shepherd |
| 2010/0151539 A1 | 6/2010 | Franklin |
| 2010/0151540 A1 | 6/2010 | Gordon |
| 2010/0151558 A1 | 6/2010 | Alianell |
| 2010/0159578 A1 | 6/2010 | Lacaze |
| 2010/0170144 A1 | 7/2010 | Day |
| 2010/0170150 A1 | 7/2010 | Walsh, Jr. |
| 2010/0196742 A1 | 8/2010 | Nealson et al. |
| 2010/0196967 A1 | 8/2010 | Edye |
| 2010/0227368 A1 | 9/2010 | Steiner |
| 2010/0233761 A1 | 9/2010 | Czartoski |
| 2010/0233787 A1 | 9/2010 | Katchanov |
| 2010/0236137 A1 | 9/2010 | Wu |
| 2010/0248333 A1 | 9/2010 | Bartilson |
| 2010/0257781 A1 | 10/2010 | Batty et al. |
| 2010/0260618 A1 | 10/2010 | Parsheh |
| 2010/0267122 A1 | 10/2010 | Chinnasamy |
| 2010/0269514 A1 | 10/2010 | Fulton, III |
| 2010/0276361 A1 | 11/2010 | Limcaco |
| 2010/0285576 A1 | 11/2010 | Norbeck |

OTHER PUBLICATIONS

Ge et al. A novel method or protein extraction from yeast using ionic liquid separation. Talanta, 81 (2010 1861-1864.*

Cheng et la. Selective extraction/isolation of hemoglobin with ionic liquid 1-butyl-3-trimethylsilylimidazolium hexafluorophosphate (BtmsimPF6). Talanta, 75 (2008) 1270-1278.*

\* cited by examiner

METHOD AND APPARATUS USING AN ACTIVE IONIC LIQUID FOR ALGAE BIOFUEL HARVEST AND EXTRACTION

This application claims the benefit of filing priority under 35 U.S.C. §119 and 37 C.F.R. §1.78 from U.S. Provisional Application Ser. No. 61/358,322 filed Jun. 24, 2010, for Method and Apparatus Using an Active Ionic Liquid for Algae Biofuel Harvest and Extraction. All information disclosed in this prior application is incorporated herein by reference.

STATEMENT REGARDING FEDERALLY SPONSORED RESEARCH OR DEVELOPMENT

The United States Government may have certain rights to the disclosed invention pursuant to Contract Number DE-SC0001306 awarded by the U.S. Department of Energy.

BACKGROUND OF THE INVENTION

1. Field of the Invention

This invention relates generally to extraction of fuel from algae. More particularly, the invention relates to use of an ionic liquid in algae biofuel harvest and/or extraction.

2. Discussion of the Related Art

Biofuel Production via Microalgal Systems

On a global scale, an alternative to fossil fuels is widely accepted as being of critical importance. Fossil fuels are a limited, nonrenewable resource that are in increasingly short supply with ever increasing demand. On a national scale, the reduction of energy dependency from foreign oil is now viewed as essential to ensure the long-term security and economic stability of the United States or any industry based country. To achieve economic sustainability as well as environmental security, fuel production processes are required that are not only renewable, but also capable of sequestering the atmospheric greenhouse gas carbon dioxide. Further, nearly all of the current renewable energy sources, such as hydroelectric, solar, wind, tidal, and geothermal, target the electricity market.

However, fuels make up a much larger share of the global energy demand. Hence, development of renewable biofuels is a strategic imperative.

Biofuel production via microalgal systems (MAS) has several competitive advantages. Algae can be the source of a wide range of feedstocks for transformation into biodiesel, green diesel, ethanol, methane, Fischer-Tropsch liquids, and hydrogen. Current supplies of biodiesel from oil crops and animal fats account for approximately 0.3% of the demand for transport fuels, thus increasing biofuel production with current technology will have severe consequences on the uses of arable land and the global food supply. In contrast, biofuel from algae can take place in non-productive lands, such as deserts and oceans, and is a non-food resource. Microalgal systems are optionally implemented in conjunction with carbon dioxide producing plants for in-situ carbon sequestration, which would be highly advantageous in a carbon cap-and-trade or carbon credit economy. Additionally, microalgal systems produce nontoxic and highly biodegradable biofuels. Still further, microalgal systems are widely regarded as one of the most efficient ways of generating biofuels, having a 50-fold increase in theoretical energy yield compared to traditional crops. Microalgal systems are the only current renewable source of oil capable of meeting the global demand for transport fuels.

Patents related to the current invention are summarized here.

Bio-Fuel Extraction

M. Cooney, et. al., "Methods and Compositions for Extraction and Transesterification of Biomass Components", U.S. patent publication no. 2009/0234146 (Sep. 17, 2009) describe methods and compositions for the direct esterification and extraction of bio-lipids and bio-oils in the production of biofuel, where the composition is an ionic liquid combined with at least one polar covalent molecule.

Dissolving Cellulose

R. Swatloski, et. al., "Dissolution and Processing of Cellulose Using Ionic Liquids", U.S. Pat. No. 6,824,599 (Nov. 30, 2004) describe dissolving cellulose without requiring the use of harmful or volatile organic solvents.

Problem

There exists in the art a need to, in an energy efficient manner, release algae constituents used in the creation of energy, fuel, nutrients, drugs, and/or cosmetic components.

SUMMARY OF THE INVENTION

The invention comprises use of a pure ionic liquid and/or an active ionic liquid to extract material from algae cells.

DETAILED DESCRIPTION OF THE INVENTION

The invention comprises use of a pure ionic liquid and/or an active ionic liquid to extract material from algae cells.

In one embodiment, a pure ionic liquid and/or an active ionic liquid is used to, in an energy efficient manner, break, dissolve, disrupt, solubilize, and/or lyse an algae cell wall, which releases algae constituents used in the creation of energy, fuel, nutrients, drugs, and/or cosmetic components.

In another embodiment, a reactor is used to extract energy or cosmetic components from harvested algae using a pure ionic liquid and/or an active ionic liquid.

Ionic Liquid

A pure ionic liquid (PIL) refers to liquids composed entirely of ions that are fluid at temperatures below about 150° C. For example, molten sodium chloride, which is commonly referred to as table salt, is not an ionic liquid in is molten form as the melting point of sodium chloride is 801° C., which is above the herein defined melting point of an ionic liquid of less than about 150° C. However, 1-butyl-3-methylimidazolium chloride, which has an anion, a cation, and a melting point of 70° C. is a pure ionic liquid when above 70° C.

Some ionic liquids are hygroscopic, which results in the hygroscopic liquids absorbing, attracting, or scavenging moisture from the air. Hence, an ionic liquid has a small percentage of water in the ionic liquid. Herein, a pure ionic liquid contain less than one-tenth of a percent water by mass. In an ionic liquid, the solvent is the salt or ions.

Conversely, an ionic solution is a solution where the solvent is water. For example, a solution of sodium chloride in water is an ionic solution. Herein, an ionic solution is a solution where water comprises 25 to 100% of the solution. An ionic solution optionally contains an inactive ionic liquid if the water concentration is greater than twenty-five percent by mass of the solution.

An active ionic liquid (AIL) refers to liquids composed primarily of an ionic salt with water comprising a smaller fraction of the liquid. Particularly, an active ionic liquid comprises 75 to 99.9% ion constituent and 0.1 to 25% water, where the ion constituent when isolated comprises a melting point of less than about 150° C. Additional soluble components are optionally present in the active ionic liquid, but the salt concentration is at least 75% of the soluble active ionic liquid components and water is less than 25% of the soluble active ionic liquid components. If an insoluble component is present, the percentages of active ionic liquid refers to the percentage of the soluble components only. For example, if insoluble, or not yet dissolved, cell walls are present, then the cell walls are not a portion of the active ionic liquid. A pure ionic liquid in a solution of 0.1 to 25% water is an active ionic liquid. A pure ionic liquid is changeable to an active ionic liquid and/or and inactive ionic solution and back, such as by the additional or removal of water.

Herein, an ionic liquid 100 refers to a pure ionic liquid in an active ionic liquid fluid.

Herein, for clarity and without limitation, 1-butyl-3-methylimidazolium chloride is used as an example of an ionic liquid 100. Many salts exist that are ionic liquids, which are usable in the methods, apparatus, and processes herein. For clarity, examples of additional ionic liquids are provided toward the end of this specification.

A 1-butyl-3-methylimidazolium chloride and water example is used to clarify the differences between a pure ionic liquid, an ionic solution or inactive ionic liquid, and an active ionic liquid. Referring now to Table 1, the percentages of 1-butyl-3-methylimidazolium chloride and water in each of a pure ionic liquid, an active ionic liquid, and an ionic solution is provided. If in the presence of un-dissolved components, then the percentages refer to only the liquid components of the solution. In the provided example, the solvent is 1-butyl-3-methylimidazolium chloride in the pure ionic liquid. Conversely, the solvent is water in an ionic solution. For the intermediate case of the active ionic liquid, the solvent is 1-butyl-3-methylimidazolium chloride, but the percentage of the 1-butyl-3-methylimidazolium chloride ranges from 75 to 99.9% of the liquid elements of the solution.

TABLE 1

Active Ionic Liquid vs. Pure Ionic Liquids and Ionic Solutions

|  | 1-butyl-3-methylimidazolium chloride Percentage | Water Percentage |
|---|---|---|
| Pure Ionic Liquid | at least 99.9% | less than 0.1% |

TABLE 1-continued

Active Ionic Liquid vs. Pure Ionic Liquids and Ionic Solutions

|  | 1-butyl-3-methylimidazolium chloride Percentage | Water Percentage |
|---|---|---|
| Active Ionic Liquid | 99.9 to 75% | 0.1 to 25% |
| Inactive Ionic Solution | less than 75% | greater than 25% |

An additional example is used to clarify an active ionic liquid. Referring now to Table 2, the percentages of ionic liquid components are provided in solutions (1) in the presence of water and (2) in the presence of both water and additional liquid components. In either case, the ionic liquid components comprise at least 75% of the solution.

TABLE 2

Active Ionic Liquid

| Component | Active Ionic Liquid and Water | Active Ionic Liquid, Water, and additional Liquid Components |
|---|---|---|
| Pure Ionic Liquid Components | 75 to 99.9% | 75 to 99.9% |
| Water | 0.1 to 25% | 0 to 25% |
| Additional Liquid Components |  | 0 to 25% |

Mixture of Ionic Liquids

Herein, an active ionic liquid refers to a single pure ionic liquid or a combination of 2, 3, 4, 5, or more separate ionic liquids. The total active ionic liquid percentage is a sum of the individual separate ionic liquid percentages in the active ionic liquid.

Ionic Liquid Structure

Figure 1:
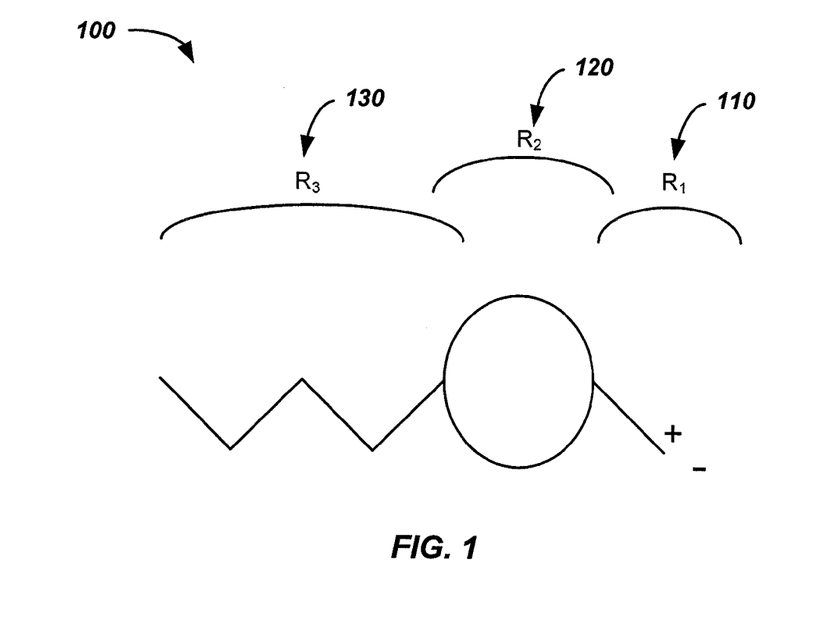
FIG. 1 figuratively illustrates a pure ionic liquid element of an active ionic liquid.
Figure 2:
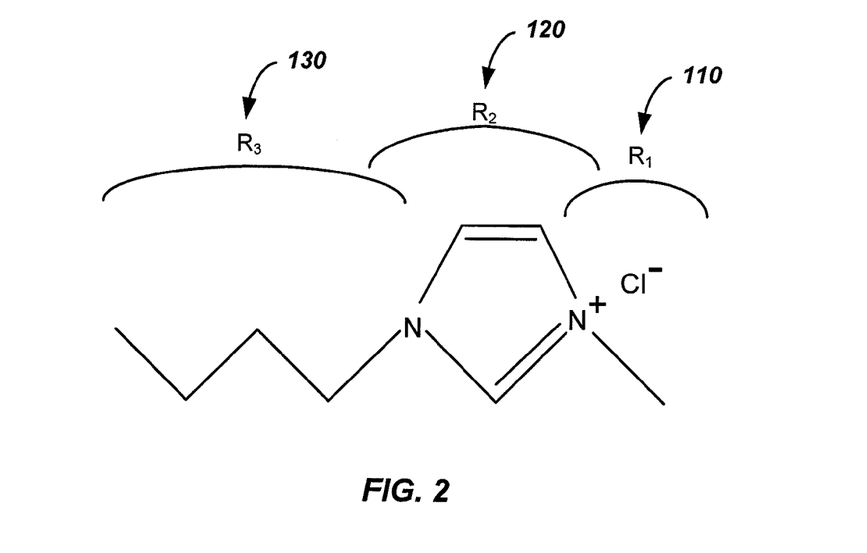
FIG. 2 provides a chemical structure of a particular pure ionic liquid element.

Referring now to FIG. 1, an ionic liquid element of an active ionic liquid 100 optionally includes three structural regions: a charge-rich region 110, $R_1$, a symmetry-breaking region 120, $R_2$, that decreases the melting point; and a hydrophobic region 130, $R_3$, that increases the melting point. Referring now to FIG. 2, each of the charge rich region 110, the symmetry-breaking region 120, and the hydrophobic region 130 of 1-butyl-3-methylimidazolium chloride, [BMIM]Cl, are illustrated. The charge-rich region 110 is optionally integrated or adjacent to one or both of the symmetry breaking region 120 or the hydrophobic region 130. Optionally, the ionic liquid 100 contains two or more charge rich regions. Optionally, one or more of the charge rich regions contains three or more charge centers, where a charge center is a negatively charged region and/or a positively charged region. A salt of 1-butyl-3-methylimidazolium is an example of a specific ionic liquid element of an active ionic liquid 100.

The salt, 1-butyl-3-methylimidazolium chloride, is an example of an ionic liquid 100. However, many ionic liquids exist and ionic liquids 100 are further described, infra.

The charge rich region 110 of the active ionic liquid 100 contains an anion and a cation. Optionally, one or more of the charge region regions 110 are present in the ionic liquid 100 and each charge rich region 110 optionally contains multiple anions and/or cations. Examples of anions include: a chloride, bromide, iodide, perchlorate, a thiocyanate, cyanate, carboxylate, or any negatively charged element or group. Examples of cations include any positively charged atom or group. Preferably, the cation is part of a ring structure, such as in the symmetry-breaking region 120. An example of a cation, which is also a symmetry breaking element is a ring structure containing nitrogen, such as any molecule having a base imidazolium ring. The symmetry breaking region 120 is optionally any structure that hinders a first ionic liquid element from laying in flat contact with a second ionic liquid element, which reduces the melting point of the ionic liquid element of an active ionic liquid 100. The hydrophobic region 130 is a $C_1$-$C_6$ alkyl group, but is optionally a carbon based chain of any length.

Ionic Liquid Melting Point

Ionic liquids are known with high melting points, such as above 150° C. Herein, the ionic liquid element of an active ionic liquid 100, hereinafter an ionic liquid 100, is preferably used in a low temperature reaction, such as below 150° C. Hence a low melting point ionic liquid is preferred, such as an ionic liquid having a melting point of less than about 150, 140, 130, 120, 110, 100, or 90 degrees centigrade. The ionic liquid 100 is also referred to herein as a molten liquid when at or above its melting point. Optionally, the ionic liquid is used herein at temperatures below the ionic liquid's melting point, such as at a glass transition temperature, where the ionic liquid contains properties that are a blend of its solid salt form and molten salt form.

Ionic liquids typically have negligible vapor pressures at operating temperatures under 150° C., are not flammable, and are thermally stable, which makes the ionic liquids suitable for low temperature extraction and/or separation techniques.

Algae and Cellulose

Algae is distinct from cellulose and recalcitrant lignocellulose. Algae does not contain lignin, which is a structural support in plant cell walls. Cellulose based plants contain lignin. Cellulose is an organic compound with the formula $(C_6H_{10}O_5)_n$, a polysaccharide consisting of a linear chain of several hundred to over ten thousand β(1→4) linked D-glucose units. Cellulose is the structural component of the primary cell wall of green plants, such as in wood or cotton. While some cellulose may be present in an algae cell wall, algae lack the various structures that characterize cellulose based land plants, such as the lignin, and phyllids, leaves, rhizoids in nonvascular plants, leaves, roots, and other organs that are found in tracheophytes, vascular plants.

Biofuel Production Using Algae

Herein, solvating, dissolving, or lysing algae is described. For clarity, lysing algae is herein described for fuel component isolation or the breaking apart of algae. Lysing refers to breaking of the cell wall. However, the techniques described herein apply to release of any algae constituent contained within an algae cell wall for use in any application, such as in energy production, to acquire starting reagents, or in the cosmetic or pharmaceutical industries.

Algae Lysing

Figure 3:
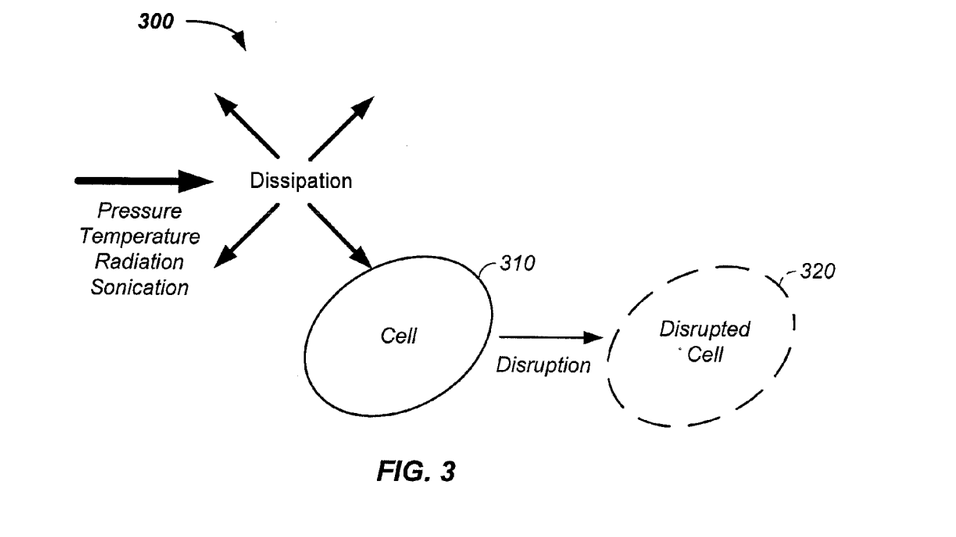
FIG. 3 illustrates cell disruption.
Figure 4:
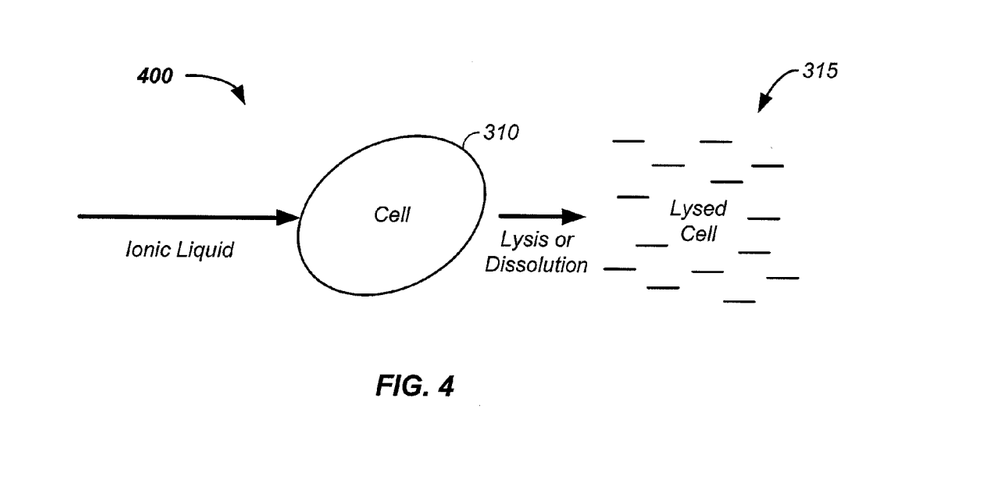
FIG. 4 illustrates cell lysis.

Referring now to FIG. 3 and FIG. 4, use of an ionic liquid 100 in the breakdown of an algae cell 310 is contrasted with use of elevated temperature, elevated pressure, sonication, and/or use of radiation in the disruption of an algae cell.

Referring now to FIG. 3, it is observed that pressure, temperature, and radiation inputs are dissipated by water about the algae cell before the algae cell is disrupted. Using pressure, temperature, and/or radiation, considerable energy is required to disrupt the cell 310. The dissipation of energy means that more energy must be put in to disrupt the cell or the matrix holding the cell needs to be treated to remove the dissipating medium. In yet another embodiment, use of an ionic liquid 100 is combined with any of pressure, temperature, and radiation inputs as the ionic liquid 100 lowers the required energy levels and the combined techniques optionally enhance processing of the algae 510.

In stark contrast, referring now to FIG. 4, in a process 400 the ionic liquid 100 contacts the cell and lyses, dissolves, degrades, or solvates the cell, which releases the cell constituents to the surrounding liquid. In the lysing process, the ionic liquid interacts with the cell walls and pulls the cell wall components into solution forming a lysed cell 315. The process of lyses or dissolution using the ionic liquid 100 has a small energy barrier compared to traditional cell disruption processes. Traditional cell disruption processes require about a mega Joule per kilogram of algae (MJ/kg). In stark contrast, the inventor has discovered processing techniques that require about a kilo Joule per kilogram of algae to lyse the algae cell wall. Generally, the traditional MJ/kg techniques are replaceable with the techniques taught herein, which require less than about 500, 400, 300, 200, 100, 90, 80, 70, 60, 50, 40, 30, 20, or 10 kJ/kg. Accordingly, the dissolution process using the ionic liquid 100 is operable at mild temperatures, such as at or below about 130, 120, 110, 100, 90, or 80° C. An ionic liquid 100 with a melting point of less that 110° C. is referred to herein as a low melting point ionic liquid. An ionic liquid 100 with a melting point of less that 90° C. is referred to herein as a very low melting point ionic liquid. An ionic liquid 100 with a melting point of less that 75° C. is referred to herein as an ultra low melting point ionic liquid. Use of an ionic liquid 100 with a lower melting point requires less energy to maintain the ionic liquid 100 at its melting point, which can aid in energy efficiency of the process 500 of converting algae 510 to product 530. Further, the dissolution process using the ionic liquid is operable at low pressures, such as at about one atmosphere, though running the process under elevated temperatures is an alternative embodiment. An ionic liquid with a melting point of greater than 150° C., such as about 200, 250, or 300° C., is referred to herein as a high melting point ionic liquid. It is understood that the melting point of an ionic liquid 100 decreases sharply in the presence of water. For clarity, herein the melting point of the ionic liquid 100 refers to the melting point of the pure ionic liquid. For example, a pure ionic liquid with a melting point of 150° C. may be fully in liquid form at a lower temperature, such as 125, 100, 75 or 50° C. However, for clarity and definiteness of description, the ionic liquid melting point of the active ionic liquid refers to the pure ionic liquid melting point.

Algae Products

Figure 5:
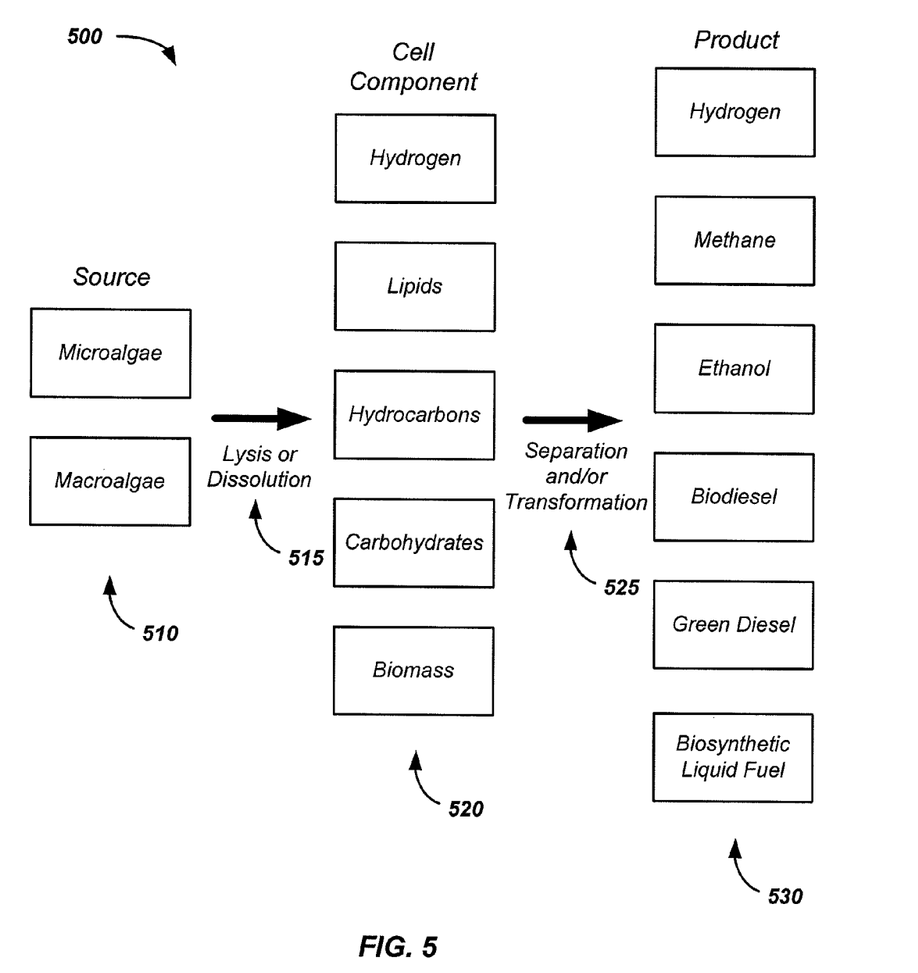
FIG. 5 provides a process of obtaining products via lysis of an algae using an ionic liquid.

Referring now to FIG. 5, a process of product creation 500 from algae 510 by the dissolution of algae 510 to release cell components 520, which are converted directly and/or directly into products 530 is described. Algae 510 refers to any of numerous groups of chlorophyll-containing, mainly aquatic eukaryotic organisms ranging from microscopic single-celled forms to multi-cellular forms. Algae is distinguished from plants by the absence of true roots, stems, and leaves. Algae phyla include: glaucophyta, chloroachniophyta, heterokontophyta, cryptophyta, dinoflagellata, haptophyta, euglenophyta, crysophyta, pyrrophyta, chlorophyta, phaeophyta, and rhodophyta. While hundreds of thousands of species of algae exist, algae herein refers to: (1) microphytes or microalgae, which are typically unicellular species existing in chains or groups in freshwater, wastewater, brackish, and marine systems and/or (2) macroalgae, which refers to large forms of algae or multi-cellular forms of algae. In a process 515, the algae 510 is dissolved by the ionic liquid 100, as described supra, resulting in cell components, such as hydrogen, lipids, hydrocarbons, carbohydrates, and biomass, to be released into the solution. Subsequently, in a process 525, the cell components are separated and/or transformed into products 530, such as hydrogen, methane, ethanol, biodiesel, green diesel, and/or biosynthetic liquid fuel.

Processes described herein operate on single cell algae species, multi-cellular species, wild type algae, engineered algae, and combination thereof.

In another embodiment, the use of the ionic liquid 100 to release cell components of an algae having a silica layer in the cell wall is described. In one example, scenedesmus, an algae, was analyzed and treated with an ionic liquid 100. The cell wall of scenedesmus has an elaborate chemical and three-dimensional structure that is uncharacteristic compared to single-cell microalgae such as chlorella or chlamydomonas. The cell wall of scenedesmus includes three layers. An inner layer is a thick layer of cellulose microfibrils bounding the coenobium. The middle layer is very thin and is made of silica. The outer layer is a very elaborate pectic layer having a system of hexagonal nets on the surface and is supported by a system of cylindrical props. At various places, the pectic layer is interrupted by circular openings. Tests reported here show that the ionic liquid 100 dissolved both the exopolysaccharide pectic layer and the inner cellulosic layer, but left the middle layer, which is a silica layer, intact. However, the silica layer is discontinuous and all or most of the algae organelles were washed out of the algae cell in the presence of the ionic liquid 100 in a period of less than about twenty minutes, which demonstrates effective lysing of the algae cell for extraction of algae constituents for fuel production. Generally, the use of an ionic liquid 100 to lyse or dissolve algae cell walls and internal components is found effective for diatoms, which are a major group of eukaryotic photosynthetic algae having large potential for lipid production. The lysing leaves the silica layer behind, but substantially lyses or dissolves the rest of the cell wall, having carbohydrates and proteins, and also lyses or dissolves elements inside the cell wall.

Reactor

Figure 6:
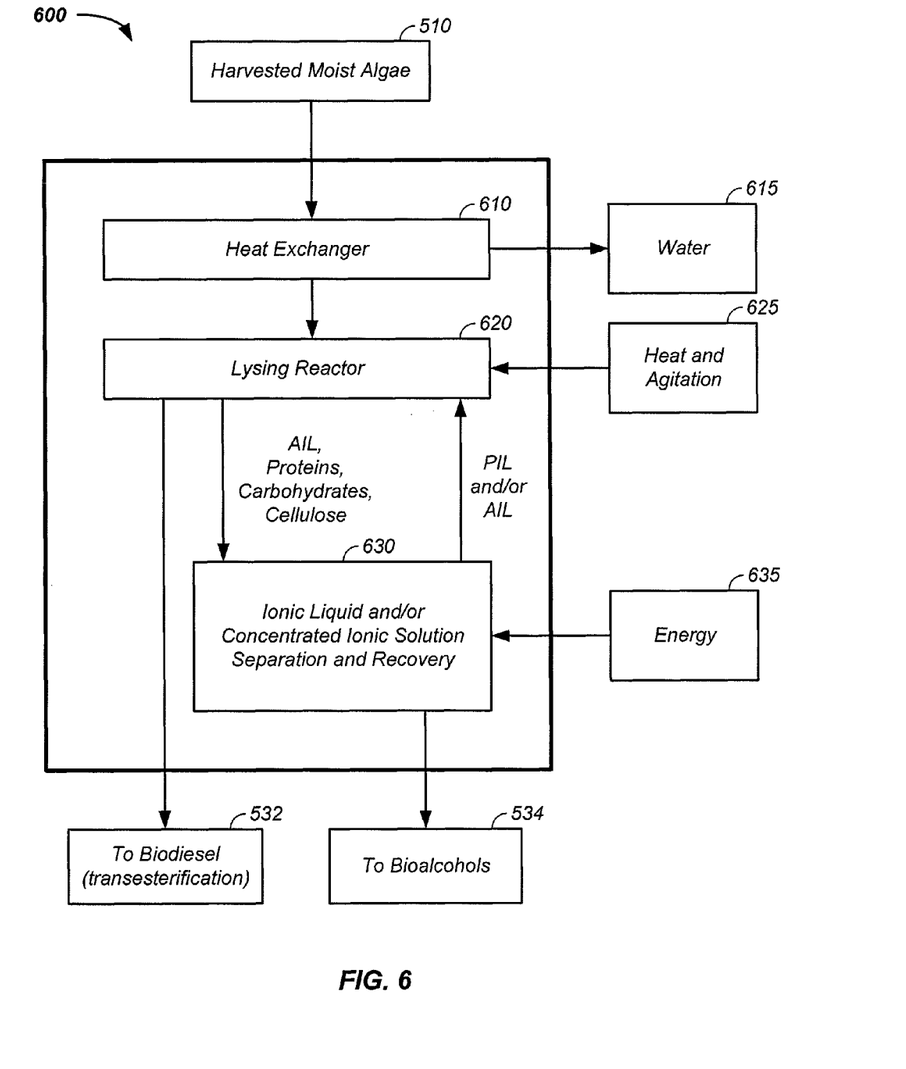
FIG. 6 provides a process of heating and lysing algae using a recoverable ionic liquid.

Referring now to FIG. 6, an overview of a reactor system 600 is provided. Any of the reactor elements or subsystems described, infra, are optionally used independently. However, the reactor elements and subsystems are preferably used together to process algae 510 to form products 530.

Reactor Overview

Generally, the reactor system 600 processes algae 510 to products 530. Algae 510 is heated in a heat exchanger 610 driving off some water 615. The heated and moist algae is subsequently lysed in a lysing reactor 620 using an active ionic liquid 100. Optionally, components of the lysing reactor 620 are heated and/or agitated 625. The ionic liquid 100 is optionally and preferably recovered 630, such as by separation, as are components dissolved in the ionic liquid. Energy 635 drives the lysing reactor 620 and/or the recovery 630. Products, 530, such as biofuels 532, biodiesel and/or bioalcohols are separated from the lysing reactor and/or ionic liquid recovery chamber. For clarity, subsystems of the reactor system 600 are described, FIGS. 7, 8, 9, and 10.

Algae Harvesting, Dewatering, and Drying

Figure 7:
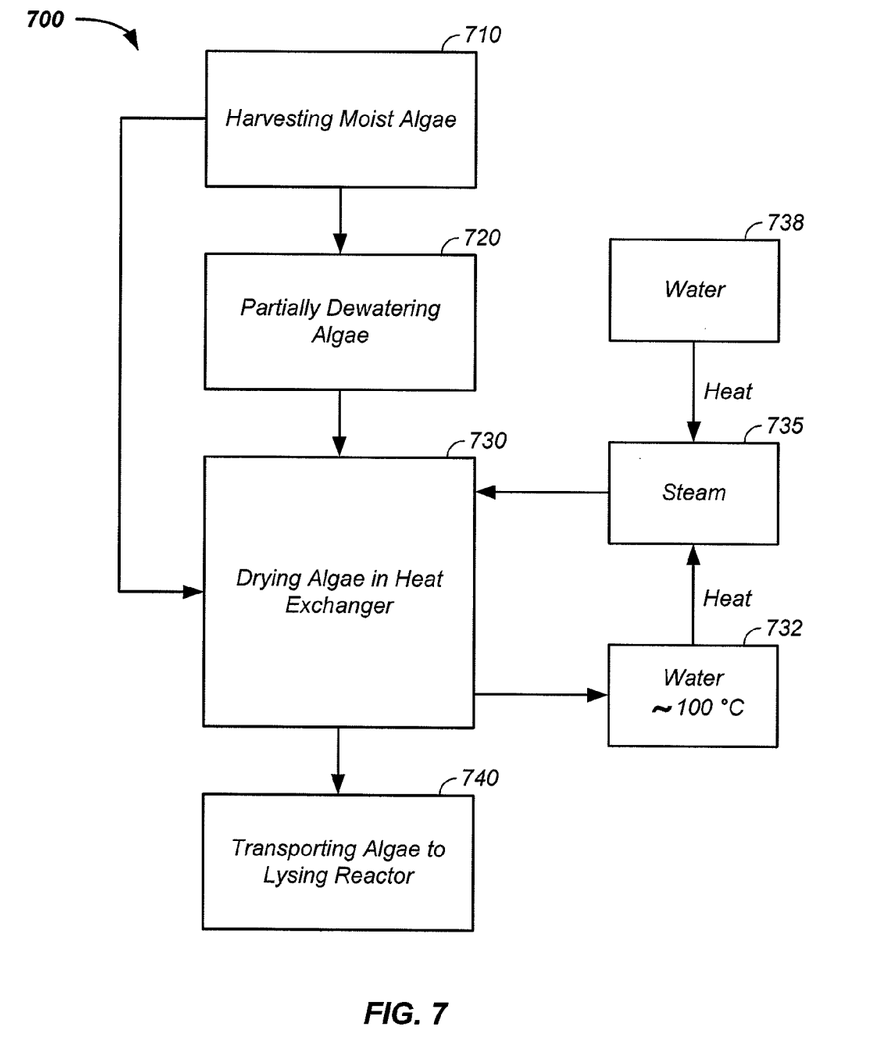
FIG. 7 provides a process for dewatering and/or drying algae.

Referring now to FIG. 7, in a process 700, algae 500 is dewatered and/or heated. The initial processing of algae 700 prior to placement in the reactor system 600 and/or after placing the algae within the reactor system 600 is further described. In a first process 710, the algae is harvested. In a second process 720, the harvested algae is preferably partially dewatered. Partial dewatering refers to increasing the solid concentration in the water from a concentration of about 0.1 to 0.15%, typical of a photoreactor or pond suspensions, up to a solid concentration of about 5, 10, or 15%. Dewatering includes a low energy input step, such as settling or filtration. In a third process 730, the dewatered algae is dried, such as in the heat exchanger 610. Herein, increasing the solid concentration of algae above about 10 or 15% is referred to as drying. Optionally, the harvested algae 510 is placed into the heat exchanger 610, either before or after dewatering. In the drying process 730, energy is used to partially evaporate water about the incoming algae 510. In one partial drying example, in a process 735, steam at about 100° C. and at about one atmosphere pressure is driven into the heat exchanger, which results in partial evaporation of water in the heat exchanger 610. The evaporated water is extracted 615 yielding water at about 100° C. Since the extracted water 615 is about 100° C., the heated water is optionally and preferably used as input water in a fourth process 735 of generating steam, which is input into the heat exchanger 610 as one energy supply of the aforementioned energy input into the heat exchanger. Optionally and typically in combination, an outside water source 738 is also converted to steam in the fourth process 735. Optionally, contents inside the heat exchanger 610 are continuously, periodically, and/or intermittently stirred or agitated, which facilitates the drying step 730. While, for clarity of presentation, steam is described as the energy source to the heat exchanger 610 in the drying process 730, any form of energy is optionally used to dry the algae, such as solar, photonic, radiant, convective, and/or electrical. In a fifth process, 740, the resulting heated and concentrated algae is moved to a lysing reactor 620, described infra. Although not preferred, the lysing step described, infra, optionally occurs in the heat exchanger 610.

Lysing

Figure 8:
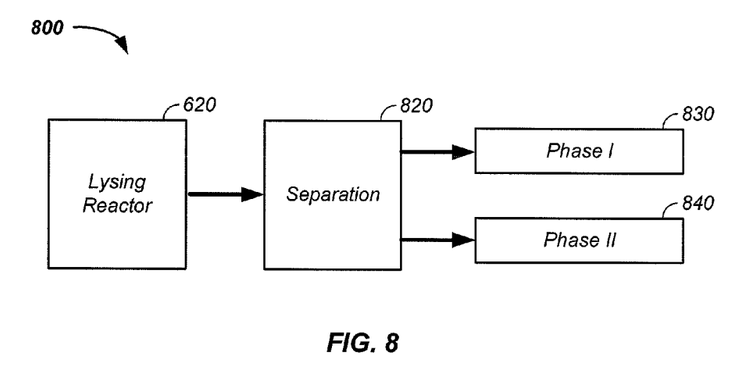
FIG. 8 provides a process of separating algae constituents.

Lysing of algae 800 in the reactor system 600 is further described. The now heated and concentrated algae is moved to the lysing reactor 620, which contains pure ionic liquid or active ionic liquid 100. Once algae is introduced into the lysing reactor, any pure ionic liquid is converted, as described supra, into active ionic liquid. The active ionic liquid 100 lyses the algae, as describes supra.

Lysing of algae 510 with an active ionic solution 100 typically occurs very rapidly, such as within a second. In a lysing reactor 620, lysing time is optionally extended, to enhance ionic liquid 100/algae 510 contact to ensure lysing, to time periods of about 1, 2, 5, 10, or 20 minutes.

The contents of the lysing reactor 620 are optionally continuously, periodically, and/or intermittently stirred and/or agitated to facilitate the lysing and/or dissolution.

Heat is optionally input into the lysing reactor 620. Preferably, the lysing reactor 620 is maintained via heat input at about 80, 90, 100, 110, 120° C. Optionally, the lysing reactor 620 is maintained at a higher temperature using any heat source, such as steam or microwave radiation. The heat of the lysing reactor 620 is optionally maintained and/or initially set at a temperature within about 5, 10, 15, or 20° C. of the melting point of the ionic liquid 100.

The pressure placed on the contents of the lysing reactor 620 is preferably about one atmosphere. However, the contents of the lysing reactor 620 are optionally maintained at higher or lower pressures, such as about 0.5, 1, 2, 3, or more atmospheres of pressure.

In various embodiments, the algae 510 is lysed using the ionic solution 100 with any combination of lysing time, agitation, heat, and/or pressure.

Product Separation

Referring now to FIG. 8, processing elements 800 of the lysing reactor 620 are described. After lying the algae 510, the lysing reactor 620 contains a plurality of lysing reactor constituents 910, such as one or more of: triacylglycerides, free fatty acids, carbohydrates, proteins, cellulose, water, the ionic liquid 100, or any other pond water or algae constituents. In a task 820, the lysing reactor constituents 910 are separated or partially separated, such as into a first phase 830 or a first state and into a second phase 840 or a second state.

Figure 9:
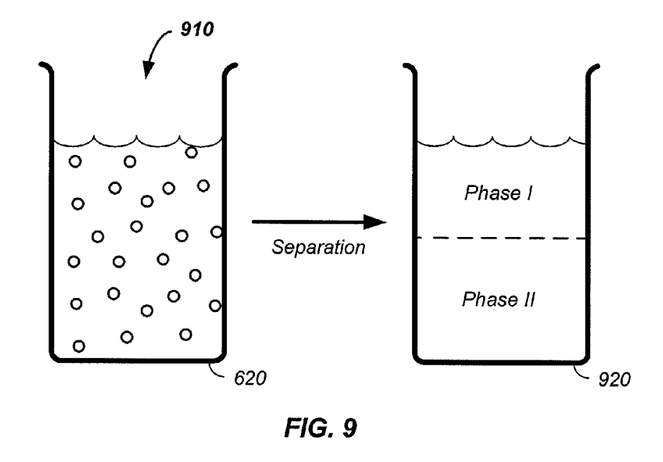
FIG. 9 illustrates separation of phases in deriving product and/or an ionic solution from lysed algae.

In a first example, the separation 820 uses chemical forces to separate the lysing reactor constituents 910, where the first phase 830 are polar compounds and the second phase 840 are non-polar compounds. Referring now to FIG. 9, the first example is illustrated figuratively and the lysing reactor constituents 910 is an emulsion of fatty elements in the ionic liquid, which spontaneously separates into an upper non-polar solution, such as fats, and a lower polar solution, such as ionic liquid 100 and water. Still referring to FIG. 9, the separation is optionally performed in the lysing reactor 620 and/or in a separate separation container or system 920.

In a second example, the separation 820 uses magnetic forces to separate the lysing reactor constituents 910, where the first phase 830 contains magnetically susceptible constituents and the second phase 840 are non-magnetic constituents.

In a third example, the separation step 820 uses density differences to separate the lysing reactor constituents 910, where the first phase 830 are lower density constituents and the second phase 840 are higher density constituents. In practice, the separation step 820 separates the constituents into any number of phases or states, not just the illustrated two phases 830, 840. Additional separation methods 820 are described, infra.

Figure 10:
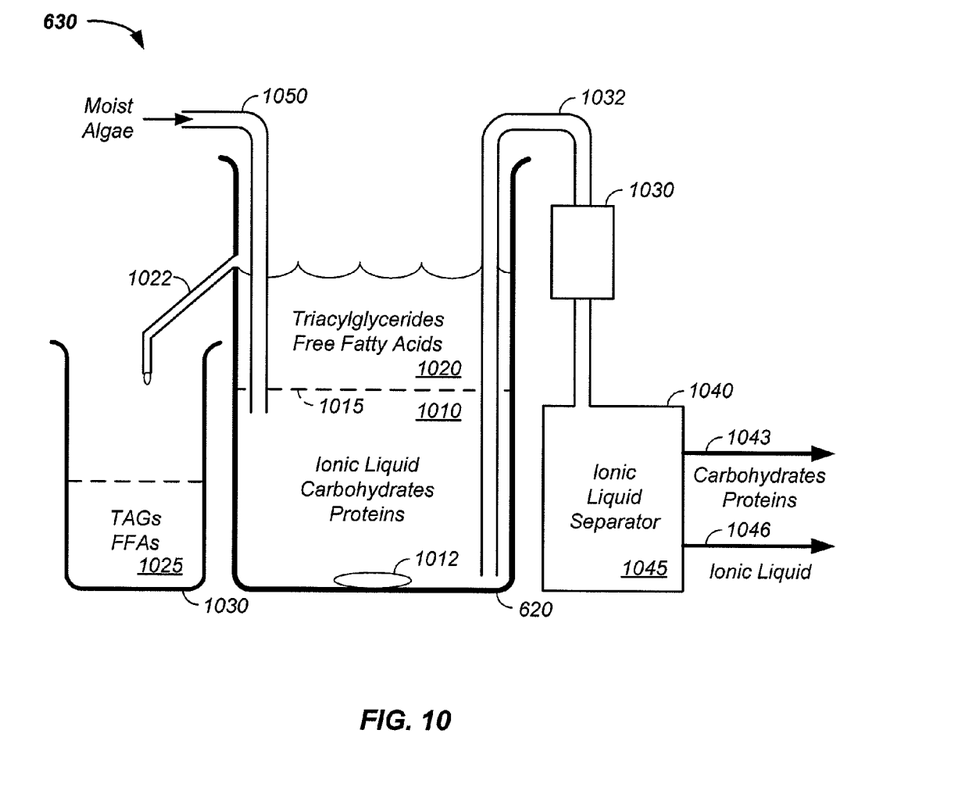
FIG. 10 illustrates separation of lysed algae constituents.

Generally, solutions, solutions with suspended particles, biphasic solutions, multiphasic solutions, and solutions with settled solids exist in one or more of the heat exchanger 610, lysing reactor 620, collection container or stream 1030, and/or an ionic liquid separator 1040, which are collectively referred to herein as ionic liquid containing solutions. Optionally, one or more of a number of separation techniques 820 are used to process any of these ionic liquid containing solutions to at least partially separate out or extract a contained constituent, such as triacylglycerides, free fatty acids, ionic liquid, carbohydrates, proteins, water, cellulose, or other pond water constituent. Separation techniques include:
- settling and decantation;
- precipitation with an organic solvent, described supra;
- formation of an aqueous biphasic solution via addition of a kosmotropic salt, described supra;
- a liquid-liquid extraction, described supra;
- foam fractionation or air flotation rising select groups to an upper surface with subsequent removal by skimming;
- electrochemical separation;
- dialysis;
- electrophoresis;
- electrofiltration;
- crystallization;
- distillation;
- thermal conversion and separation;
- enzymatic conversion and separation;
- adsorption;
- chromatography moving a mixture dissolved in a mobile phase through a stationary phase;
- centrifugation;
- ultrafiltration;
- flocculation;
- stripping;
- a separation using a magnetic field to extract magnetically susceptible solute molecules or structures; and
- a low Energy process taking less than about 1 MJ/kg, 500 kJ/kg, 100 kJ/kg, 10 kJ/kg, or 1 kJ/kg of total solute.

To further clarify, additional separation techniques 820 are described, infra.

Specific Gravity and/or Solubility Separation

Lipids have 0.2 to 0.4 lower specific gravities than 1-butyl-3-methylimidazolium chloride. In addition, 1-butyl-3-methylimidazolium chloride is hydrophilic and lipophobic. Hence lipids spontaneously phase-separate from the ionic liquid 100. It is clear that as the cell wall is removed, lipid vesicles present inside the cell are freed, forming emulsion droplets in the ionic liquid 100, which can spontaneously coalesce to form one layer or phase 830 at the top of the reaction mixture and the ionic liquid will form a second layer or phase 840 below the spontaneously formed lipophilic layer. Other cell constituents are either dissolved in the ionic liquid 100 or precipitate out of solution.

Liquid/Liquid Extraction Based Separation

In some cases, the emulsion 910 is stable, for instance due to interaction with surfactants also present in the cell. If lipid emulsions are sufficiently stable, a liquid-liquid (L-L) extraction step for the lipid is optionally used. In this example, the ionic liquid lysate solution from the dissolution and/or lysis is treated with a liquid-liquid extraction step. In the liquid-liquid extraction step, the liquid extractant is brought into contact with the emulsified lipid to extract the lipid components from the ionic liquid based solution. In one case, the extractant is the same lipid produced by algae due to its poor miscibility in ionic liquid, which is much less than 1%, and is an exact polarity match resulting in maximizing extraction efficiency. Optionally, any lipophilic solution is used as the extractant, such as an organic solvent. Similarly, the extractant is optionally hydrophilic and is used to extract the ionic liquid 100. For example, the extractant is a second distinct ionic liquid.

A specific example of lysing of algae 510 and product separation is further described. In practice, the lysing and separation steps are optionally done on an industrial scale in a continuous flow system, an intermittent flow system, and/or in a batch system. Referring now to FIG. 10, for clarity, an example of a separation processes using laboratory type equipment is illustrated figuratively. As described, supra, the lysing reactor 620 contains the heated and partially dried algae 510 and the ionic liquid 100. Upon lysing and/or dissolution of the algae, the lysing reactor contains triacylglycerides, free fatty acids, carbohydrates, proteins, cellulose, water, and/or the ionic liquid 100. Additional components of lesser concentration are optionally present in the lysed solution 315. Herein, a triacylglyceride (TAG) or triacylglycerol is an ester composed of a glycerol bound to three fatty acids, which is a constituent of algae, vegetable oil, and/or animal fats. In the lysing reactor, or any container to which the lysed components are transferred, the lysed solution spontaneously separates based on density, such as into two or more layers or phases. Generally, the ionic liquid 100 and/or hydrophilic constituents settle toward the bottom to form a lower layer 1010, which in an example of a first phase 830, and hydrophobic and/or ionic liquid phobic constituents rise toward the top of the reaction mixture to form an upper layer 1020, which is an example of a second phase 840. A phase or density separation or partial separation layer 1015 forms a partial boundary between the lower layer 1010 and upper layer 1020. In practice, multiple density layers are optionally formed. Examples of constituents in the upper layer include the triacylglycerides and/or the fatty acids. Examples of constituents in the lower layer include the ionic liquid(s) 100, the carbohydrates, the proteins, the cellulose, and the water. It is observed that the lower density constituents in the upper layer 1020 are readily removed, such as via an overflow 1022, via a mechanical pump pulling from the upper layer 1020, via decanting, or by any automated or manual removal of at least a portion of the upper layer 1020 to a collection container or stream 1030, which contains lower density constituents 1025, such as the triacylglycerides and/or free fatty acids. Similarly, the higher density constituents in the lower layer 1010 are readily removed, such as via a mechanical pump 1030 pulling from the lower layer 1010, via decanting and keeping the lower layer 1010, or by and automated or manual removal of at least a portion of the lower layer 1010 to a second container, stream, or ionic liquid separator system 1040, which contains higher density constituents 1045, such as the ionic liquid 100, carbohydrates, proteins, cellulose, and/or water. The ionic liquid concentration and product recovery system 630 is optionally continuously run by providing a semi-dry algae stream 1050 to the lysing reactor 620. The solution in the lysing reactor is optionally continuously, periodically, or discontinuously stirred and/or agitated with a stirrer 1012. Components in the upper layer collection container or stream are optionally further processed, such as by transesterification to form biodiesel. Notably, the lower density constituents 1025 are optionally available in the collection container or stream 1030 at about 100° C., which is an adequate starting temperature for the transesterification process.

Ionic Liquid Recovery

The ionic liquid separator 1040 of the ionic liquid separation and/or recovery process 630 is further described. Generally, any of the separation techniques, described supra, used in separation of the lysing reactor 620 constituents 910 are used in the ionic liquid separation and/or recovery process 630, in which generally:

ionic liquid is recovered; and/or carbohydrates, proteins, cellulose, and/or water are separated.

Optionally, the separation step 820 occurs prior to or at the same time as the ionic liquid separation and/or recovery process 630. Examples are provided of processes used in the ionic liquid separator step 740 as part of the ionic liquid separation and/or recovery process 630.

In a first example of ionic liquid recovery, the ionic liquid 100 is recovered through the addition of salt. In one case, a kosmotropic salt is added to the collected ionic liquid containing solution. Particularly, separation of the ionic liquid 100 is achieved through the formation of an aqueous biphasic system (ABS). Hydrophilic ionic liquids 100, such as 1-butyl-3-methylimidazolium chloride, form an aqueous biphasic system upon addition of a salt, such as any of $K_3PO_4$, KOH, $K_2CO_3$, $Na_2HPO_4$, and $Na_2S_2O_3$. The process is referred to herein as salting out. In salting out, addition of a suitable concentrated salt introduces electrostatic and/or hydrophobic forces that spontaneously separate the solution into an ionic liquid-rich and a salt-rich phase. These two phases, in turn, separate-out species present in the original solution before salting out. For instance, substances more soluble in water tend to stay in the water phase and substances more soluble in the ionic liquid tend to stay in the ionic liquid phase. Optionally, the exploitation of aqueous biphasic system formation on the ionic liquid/water solutions takes place in liquid-liquid extraction steps, as described supra. Optionally, the extraction of the ionic liquid 100 is achieved using ion exchange extraction and/or ion pair extraction.

In a second example, an organic solvent is used to precipitate a constituent of the ionic liquid containing solution, such as precipitation of carbohydrates, celluloses and/or proteins. The removal of the precipitate results in a renewed or concentrated ionic liquid 100. Examples of organic solvents used to precipitate a liquid constituent include: methanol, methanol/water mixtures, chloroform, dichloromethane, or ethyl acetate. Optionally, this, or any of the extraction techniques described herein, are performed in a continuous solid-liquid or liquid-liquid extraction step, such as with the volatile organic or volatile organic chemical input.

In a third example, a physical property of the particular ionic liquid 100 to be separated is used in the separation process.

Harvesting Algae Biofuel

In yet another embodiment, use of an ionic liquid to aid in recovery of an algae component is combined with any other algae constituent extraction technique, such as use of solar, ultrasound, elevated temperature, elevated pressure, sonication, microwave heating, and/or radiation.

Figure 11:
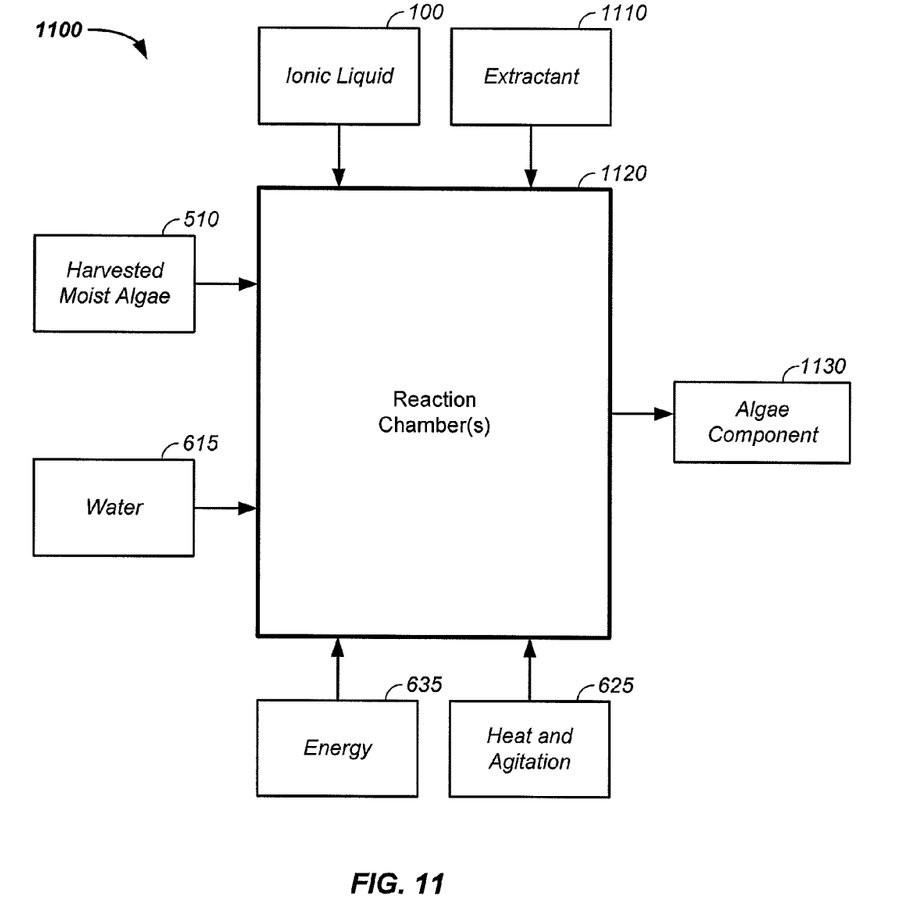
FIG. 11 illustrates a reactor system for converting algae to an algae component and/or product.

Referring now to FIG. 11, a reactor system 1100 for converting algae 510 to an algae component 1130 and/or product 532 is illustrated. One or more of the ionic liquid 100, and extractant 1110, water 615, energy 635, and heat and agitation 625 are added to the reaction chamber 1120 and at least one algae component is extracted.

Although the invention has been described herein with reference to certain preferred embodiments, one skilled in the art will readily appreciate that other applications may be substituted for those set forth herein without departing from the spirit and scope of the present invention.

What is claimed is:

1. A method for extracting material from algae cells comprising lysing the cell walls of the algae cells by contacting the algae cells to a first liquid selected from a group consisting of a pure ionic liquid and an active ionic liquid, wherein the algae cells are in the form of a water suspension.

2. The method according to claim 1 wherein the pure ionic liquid includes less than 0.1% water and at least 99.9% of an ionic salt having a melting temperature below about 150° C.

3. The method according to claim 1 wherein the cell walls are lysed in the absence of a co-solvent.

4. The method according to claim 1 wherein the active ionic liquid includes 0.1% to 25% water and 75% to 99.9% of an ionic salt having a melting temperature below about 150° C.

5. The method according to claim 1 wherein the water suspension includes a solid concentration of algae cells of about 0.1 to 0.15%.

6. The method according to claim 1 wherein the water suspension includes a solid concentration of algae cells of up to about 15%.

7. The method according to claim 1 wherein lysis of the cell walls of the algae cells requires less than about one kilo Joule per kilogram of algae.

8. The method according to claim 7 wherein the temperature of the first liquid is below about 130° C.

9. The method according to claim 1 further comprising releasing the material from the algae cells into the first liquid, dissolving the material into the first liquid and separating the material from the first liquid.

10. A method for processing algae cells comprising, introducing a water suspension of algae cells into a lysing reactor containing a first liquid selected from a group consisting of a pure ionic liquid and an active ionic liquid, lysing the cell walls of the algae cells by contacting the algae cells to the first liquid, forming within the reactor a lysed solution containing the first liquid, water and algae cell-derived materials including triacylglycerides, free fatty acids, carbohydrates, proteins, and/or cellulose, and separating the lysed solution into at least two layers including an upper layer and a lower layer.

11. The method according to claim 10 further comprising fanning a partial separation layer situated between the upper layer and the lower layer.

12. The method according to claim 10 wherein the upper level includes the triacylglycerides and/or the free fatty acids.

13. The method according to claim 10 wherein the lower level includes the first liquid, the carbohydrates, the proteins, the cellulose and the water.

14. The method according to claim 10 further comprising separating the upper layer from the lower layer.

15. The method according to claim 14 further comprising introducing the lower level of the lysed solution into an ionic liquid separator configured for separating the first liquid from the algae cell-derived materials.

16. The method according to claim 15 wherein the ionic liquid separator relies upon the addition of salt to the lower level of the lysed solution to separate the first liquid from the algae cell-derived materials.

17. The method according to claim 16 wherein the salt is a kosmotropic salt.

18. The method according to claim 15 wherein the ionic liquid separator relies upon the addition of an organic solvent to the lower level of the lysed solution to separate the first liquid from the algae cell-derived materials.

19. The method according to claim 10 wherein the cell walls are lysed in the absence of a co-solvent.

20. The method according to claim 10 wherein the water suspension includes a solid concentration of algae cells of up to about 15%.

* * * * *